(12) United States Patent
Yang et al.

(10) Patent No.: US 12,090,265 B2
(45) Date of Patent: Sep. 17, 2024

(54) ULTRASONIC ELECTRONIC RHINITIS THERAPEUTIC APPARATUS WITH FAR-INFRARED ATOMIZED COCONUT ESSENTIAL OIL

(71) Applicant: Cartean (Henan) Technology Co., Ltd., Zhengzhou (CN)

(72) Inventors: Fujun Yang, Zhengzhou (CN); Hongjun Yang, Zhengzhou (CN); Xiaoqi Du, Zhengzhou (CN); Rong Wang, Zhengzhou (CN)

( * ) Notice: Subject to any disclaimer, the term of this patent is extended or adjusted under 35 U.S.C. 154(b) by 549 days.

(21) Appl. No.: 17/478,961

(22) Filed: Sep. 20, 2021

(65) Prior Publication Data

US 2023/0088806 A1   Mar. 23, 2023

(51) Int. Cl.

| | |
|---|---|
| *A61M 11/04* | (2006.01) |
| *A61K 31/20* | (2006.01) |
| *A61K 36/888* | (2006.01) |
| *A61M 15/00* | (2006.01) |
| *A61M 15/08* | (2006.01) |

(52) U.S. Cl.
CPC ............ *A61M 11/041* (2013.01); *A61K 31/20* (2013.01); *A61K 36/888* (2013.01); *A61M 15/0085* (2013.01); *A61M 15/08* (2013.01); *A61M 2205/368* (2013.01); *A61M 2210/0618* (2013.01)

(58) Field of Classification Search
CPC ........ A61M 11/00–001; A61M 11/005; A61M 11/04–042; A61M 15/00–0001; A61M 15/0005; A61M 15/001; A61M 15/0028; A61M 15/0065; A61M 15/0068; A61M 15/008; A61M 15/0083–0085; A61M 15/08–085; A61M 2205/368; A61M 2210/0618; A61K 31/20; A61K 36/888
See application file for complete search history.

(56) References Cited

U.S. PATENT DOCUMENTS

| | | | |
|---|---|---|---|
| 6,196,218 B1 * | 3/2001 | Voges ..................... | A24F 40/48 128/200.14 |
| 8,985,100 B2 * | 3/2015 | Minocchieri ......... | A61M 16/00 128/203.12 |
| 2019/0314586 A1 * | 10/2019 | Minskoff .......... | A61M 15/0066 |
| 2020/0170301 A1 * | 6/2020 | Gallagher ............. | A24F 40/485 |

\* cited by examiner

*Primary Examiner* — Rachel T Sippel

(57) ABSTRACT

An ultrasonic electronic rhinitis therapeutic apparatus with far-infrared atomized coconut essential oil is disclosed. The apparatus includes a nasal plug part and a nasal alar part. The nasal plug part includes an insertion column disposed in a nostril. The insertion column is internally provided with a coconut powder, and a far-infrared generating tube is arranged in the coconut powder. An ultrasonic generator is arranged in the nasal alar part, and the nasal alar part is fitted on the lateral side of the nasal alar. In the disclosure, the oil and acid substance in the coconut powder are atomized by far-infrared light and are atomized under the aid of pulse ultrasonic wave in the nasal cavity to be inhaled into the internal tissues of the nasal cavity, sinus and the like.

10 Claims, 3 Drawing Sheets

ULTRASONIC ELECTRONIC RHINITIS THERAPEUTIC APPARATUS WITH FAR-INFRARED ATOMIZED COCONUT ESSENTIAL OIL

TECHNICAL FIELD

The present disclosure relates to the technical field of electronic medical products, and more specifically, to an ultrasonic electronic rhinitis therapeutic apparatus with far-infrared atomized coconut essential oil.

BACKGROUND ART

Infrared rays are usually applied in medical or industrial fields for their better heat effects than the visible or ultraviolet rays, and can be used for disinfection, sterilization, joint and muscle treatment. The infrared rays with the shortest wavelength is the far-infrared rays, which can penetrate 4 to 5 centimeters below the skin, has good heat transfer effect, and generates adenosine-triphosphate (ATP) and nitric oxide, thus having a remarkable effects on the treatment of diseases.

In terms of the process of causing rhinitis, antibodies are produced by B lymphocytes, which plays a key role in the body's immune response and the T cells play an auxiliary role. The produced antibodies react with an allergen and an antigen antibody, and then the allergen is introduced to combine with the antibodies of mast cells to cause an antigen-antibody reaction, and a histamine is released to cause an allergic reaction. The commonly taken anti-inflammatory agents have the effects of inhibiting a histamine.

Based on the clinical trials related to the influence of far infrared rays on allergic rhinitis, 24 mice were used as experimental subjects, and the subjects were irradiated with low power laser within 7 days, and the results were tested. The hematoxylin-eosin (HE) staining was performed to observe the tissue changes of nasal cavity: in control group (b), the number of inflammatory cells in nasal septum epithelium was higher than that in normal group (a). Low power laser group (c) and high power laser group (d) not only recovered epithelial damage, but also significantly reduced the number of inflammatory cells infiltrating epithelium. Especially in the low-power investigation group of 1000 mj, the laser effect is more remarkable than the high-power effect.

In the existing products, the infrared generator is only applied on the nose in the way of internal, external and internal and external, which can only reach the nasal vestibule and nasal valve, but cannot reach the upper, middle and lower nasal passages, and even less the sinuses. The treatment of nasal cavity and posterior chamber is even less. In addition, the volatilization of traditional Chinese medicine rhinitis plug is not strong. The defect of nasal drops is that the drug stays for a short time and quickly flows out with the nose. Many patient representations, cleaning with a nasal saline spray can relieve allergic symptoms because the nasal saline spray can dilute the stimulus and mitigate corresponding effects. If saline spray can't alleviate the disease, cleaning is also feasible. Cleaning is usually to clean the nasal tubes and sinuses with solution. However, cleaning is only effective for severe non-allergic rhinitis, and these patients usually secrete viscous mucus which is difficult to excrete. These drugs can't go deep into various tissues of nasal cavity for a long time and carry out systematic repair. The effect of washing spray alone and infrared therapy is limited.

Therefore, providing an ultrasonic electronic rhinitis therapeutic apparatus with far-infrared atomized coconut essential oil becomes an urgent problem for those skilled in this field.

SUMMARY

In view of this, the present disclosure provides an ultrasonic electronic rhinitis therapeutic apparatus with far-infrared atomized coconut essential oil. The oil and acid substances in the coconut powder are volatilized in the nasal cavity through an infrared light atomization, and combined with the auxiliary atomization effect of pulse ultrasonic wave. It is used for treating chronic rhinitis, acute rhinitis, sinusitis, nasal polyps, and the like.

In order to achieve the above purpose, the following technical schemes are adopted.

An ultrasonic electronic rhinitis therapeutic apparatus with far-infrared atomized coconut essential oil, comprising a nasal plug part and a nasal alar part;

wherein the nasal plug part includes an insertion column disposed in a nostril, the insertion column is internally provided with a coconut powder, and a far-infrared generating tube is arranged in the coconut powder;

wherein an ultrasonic generator is arranged in the nasal alar part, and the nasal alar part is fitted on the lateral side of the nasal alar.

The disclosure provides a wearable nose plug with controlled function. A columnar far-infrared ray generating tube coated with a graphene near red generating film is placed in coconut powder, and chronic rhinitis, acute rhinitis, nasosinusitis, nasal polyp and so on are treated by the volatilization of effective components in the nasal cavity of the atomized coconut powder and the assistance (standard: 1.5 MHz pulse, pulse width of 200 μs, intensity of 30 mW/cm2 at 1 kHz) of low intensity pulsed ultrasound (LIPUS). The oil and acid substances in the coconut can be atomized (especially lauric acid), the atomization effect enables grease and acidic substances in the coconut to be more easily diffused in the nasal cavity, meanwhile, the auxiliary treatment effect of infrared rays is combined to help to exert the effects of detumescence of coconut oil, especially lauric acid, detumescence and nasal mucosa inflammation, repairing nasal mucosa and improving nasal mucosa immunity.

Preferably, two insertion columns are provided, and arranged in two nostrils respectively. The far-infrared generating tube is arranged at the middle position of the insertion column, which is more beneficial for the coconut powder inserted into the column to receive the radiation from the far-infrared generating tube evenly, thereby improving the utilization rate and utilization effect of the coconut powder.

Preferably, the insertion column includes a coconut powder sleeve. The coconut powder sleeve is a hollow cylindrical bag. The hollow cylindrical bag is filled with coconut powders, and the far-infrared generating tube is provided at the hollow position of the hollow cylindrical bag. The coconut powder sleeve is more beneficial for cleaning the far-infrared generating tube and is easy for replacing the coconut powder.

Preferably, the material of the hollow cylindrical bag includes polyethylene terephthalate (PET) non-woven fabric, and is made by sealing and pressing with a sealing press, and is sleeved at the bottom of the far-infrared generating tube for packaging. The bottom part is an end part inserted into a nostril.

Preferably, the outer surface of the far-infrared generating tube is coated with a graphene far-infrared film, so that the infrared radiation power can be increased, and the atomization effect can be improved by 45% according to experiments.

Preferably, the far-infrared generating tube is connected with a screw thread base, and the screw thread base is provided with a circuit connection point.

Preferably, the nasal alar part further includes a connecting part. The insertion column is arranged vertically on the connecting part. The arrangement of the connecting part makes the disclosure more convenient to wear. The insertion column is not easy to slip off after wearing, and the fixing ability is better. The insertion column is detachably connected. The nasal alar part is connected to the top end of the connecting part and is provided with two parts which are fitted on the two sides of the outer part of the nasal alar, and the structural position of the nasal alar part and the connecting part are arranged in a manner of meeting the ergonomic design so that the structure is more comfortable and the wearing is firmer, which can ensure that the far-infrared generating tube and the ultrasonic generator act in an effective position and improve the treatment effect.

Preferably, the coconut powder is placed in a hollow cylindrical bag. One end of the hollow portion of the hollow cylindrical bag has an opening. The other end of the hollow cylindrical bag is closed, and the far-infrared generating tube is directly sheathed through the opening of the hollow cylindrical bag when in use. A new coconut powder sleeve is replaced each time of use.

Preferably, the two ends of the connecting part along the lateral corresponding direction of the nostril are provided with wearing fixing holes, which can be used for connecting the wearing string.

Preferably, it further includes an external control circuit. The external control circuit is electrically connected with the far-infrared generating tube and the ultrasonic generator, and is configured to supply power to the far-infrared generating tube and the ultrasonic generator, and perform timed counting.

Preferably, the ultrasonic electronic rhinitis therapeutic apparatus is used for atomizing an atomized grease and acid of coconut powder, and the acid includes lauric acid.

According to the technical scheme, compared with the prior art, the beneficial effects of the disclosure are:

In this disclosure, chronic rhinitis, acute rhinitis, nasosinusitis, nasal polyps and the like are treated by atomizing the drug components in the coconut powder under the atomization and irradiation of infrared light and the assistance of ultrasonic waves in the nasal cavity. The far-infrared light generator heats the powder and carries out infrared treatment on the patient's nasal cavity at the same time, and the medicine heated by infrared light will bring the heated volatilized substances into the nasal tissue along with the patient's nasal breath. Low intensity pulsed ultrasound can accelerate drug atomization and promote tissue recovery at the same time, the treatment of far-infrared light and lauric acid play a complementary role.

The atomized coconut oil and lauric acid can reduce the inflammation of nasal mucosa, repair the nasal mucosa, and improve the immune function of nasal mucosa. Improve the tissue recovery ability of nose itself, thus changing some long-term, chronic and recurrent rhinitis symptoms fundamentally. At the same time, the heated drug is good in effect, fast in absorption, and small in irritation to tissues such as mucous membranes in the nasal cavity.

BRIEF DESCRIPTION OF THE DRAWINGS

In order to explain the embodiment of the present disclosure or the technical scheme in the prior art more clearly, the drawings used in the embodiment or the description of the prior art will be briefly introduced below. Obviously, the drawings in the following description are only embodiments of the present disclosure, and for ordinary technicians in the field, other drawings can be obtained according to the provided drawings without paying creative effort.

DETAILED DESCRIPTION OF THE EMBODIMENTS

Figure 1:
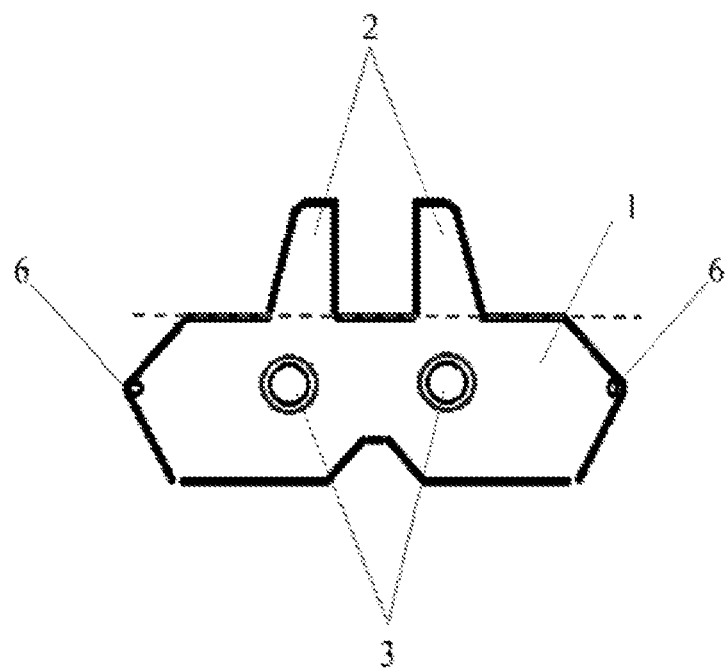
FIG. 1 is a structural diagram of an ultrasonic electronic rhinitis therapeutic apparatus with far-infrared atomized coconut essential oil provided by an embodiment of the present disclosure.
Figure 2:
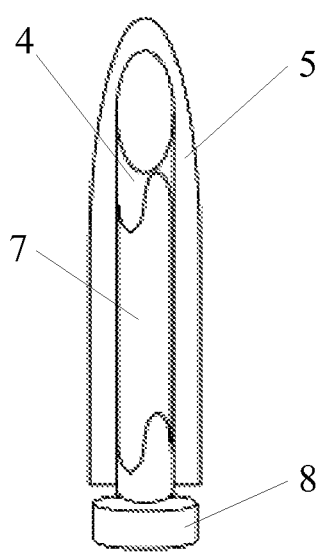
FIG. 2 is a structural diagram of an insertion column provided by an embodiment of the present disclosure.

The following will clearly and completely describe the technical scheme in the embodiments of the present disclosure with reference to the drawings in the embodiments of the present disclosure. Obviously, the described embodiments are only parts of the embodiments of the present disclosure, but not all of them. Based on the embodiments of the present disclosure, all other embodiments obtained by a person of ordinary skill in the art without creative efforts are within the scope of the present disclosure.

An ultrasonic electronic rhinitis therapeutic apparatus with far-infrared atomized coconut essential oil is disclosed, which belongs to a wearing electronic rhinitis therapeutic apparatus. The apparatus includes a nasal plug part and a nasal alar part 2. The nose plug part includes an insertion column 3 disposed in a nostril. The insertion column 3 is internally provided with a coconut powder. A far-infrared generating tube 4 is provided in the coconut powder. An ultrasonic generator is arranged in the nasal alar part 2, and the nasal alar part 2 is fitted on the lateral side of the nose alar. The far-infrared generating tube 4 is inserted into a medicine bag with coconut powder, and the nasal alar part 2 encapsulates low intensity pulsed ultrasound (LIPUS).

In one embodiment, the ultrasonic electronic rhinitis therapeutic apparatus is used for atomizing a grease and acid of coconut powder. By atomizing the grease and acid (mainly lauric acid) in the coconut powder into nasal sinus energy internal tissue, a continuous, stable and low-stimulation drug supply treatment method is provided for the tissue.

This embodiment solves the following problems: 1. The disadvantage of single therapeutic effect of infrared rhinitis therapeutic apparatus; 2. The disadvantage of rhinitis irrigator spray cannot be used continuously; 3. The characteristic of nasal hypersensitivity and inability to use large amounts of medication; 4. Complex nasal cavity structure and a single drug cannot solve the problem of multi-site lesions; 5. Unable to effectively treat inflammation or enlargement problems of nasal cavity, nasal sinus and nasal polyp.

In use of this embodiment, the insertion column 3 is placed in the nostril, and then the nasal alar part 2 is fitted on the nasal alar to open the far-infrared generating tube 4.

The far-infrared ray irradiates the coconut powder in the insertion column 3 and effective medicine components in the coconut powder are volatilized. At the same time, under the atomization of the ultrasonic generator, the effective medicine components are further accelerated to be atomized, and are fully diffused to various tissues in the nose along with the respiratory action, thereby keeping the retention time of the medicine in the nasal cavity and improving the treatment effect.

In one embodiment, the far-infrared generating tube 4 with the wavelength of 8-15 microns is selected. The far-infrared generating tube 4 is provided at the middle position of the insertion column 3, and the coconut powder in the insertion column 3 is more beneficial to uniformly receiving the irradiation of the far-infrared generating tube 4.

In one embodiment, the insertion column 3 includes a coconut powder sleeve in the form of a hollow cylindrical bag 5 filled with coconut powder 10. The far-infrared generating tube 4 is placed at the hollow position of the hollow cylindrical bag 5.

In the implementation of the embodiment, the update and replacement of the product can be completed by replacing the coconut powder cover, and when the current coconut powder is used up, the whole electronic rhinitis therapeutic apparatus is not required to be replaced, and only a new coconut powder sleeve is required to be replaced, so that the cost of the product is reduced, and the convenience for using and updating the product is increased.

Figure 3:
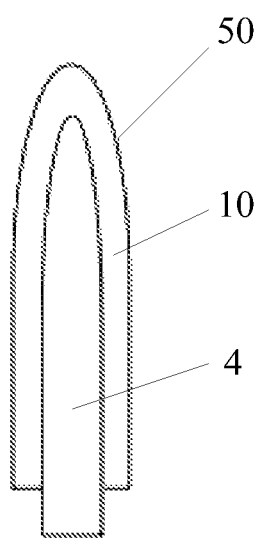
FIG. 3 is a structural diagram of a hollow cylindrical bag provided by an embodiment of the present disclosure.

In one embodiment, referring to the FIG. 3, the material of the hollow cylindrical bag 5 includes a Polyethylene terephthalate (PET) non-woven fabric 50, and is made by sealing and pressing with a sealing press, and is sleeved at the bottom of the far-infrared generating tube for packaging. The bottom part is an end part inserted into a nostril.

Specifically, referring to the FIG. 3, a hollow cylindrical bag 5 is filled with coconut powder 10. The preparation processes of the powder are as follows: coconut is air-dried at low temperature and crushed to 50 meshes. The coconut powder was filled into the hollow cylindrical bag 5 (air permeability 41.21/sq.m/sec,196 Pa, thickness 0.19 mm) of PET food grade non-woven fabric. The packaging structure of the hollow cylindrical bag 5 is as follows: after the hollow cylindrical bag 5 is filled, a non-woven fabric bag 50 with a thickness of 0.25 cm and a width of 2.3 cm is used for packaging by using a sealing press and is screwed into a cylinder with a diameter of 1 cm and a length of 2.3 cm and a space with a little space. A far-infrared light generator is arranged in the middle and the bottom is packaged.

In one embodiment, the outer surface of the far-infrared generating tube 4 is coated with a graphene far-infrared film 7.

In one embodiment, the bottom of the far-infrared generating tube 4 is connected with a screw thread base 8. The screw thread base is provided with a circuit connection point.

In one embodiment, the nasal alar part 2 further includes a connecting part 1. The insertion column 3 is arranged vertically on the connecting part 1. As shown in FIG. 1, the shape of the connecting part 1 is matched to the shape of the nose front end surface. The fitting property is enhanced, and the position of the insertion column 3 corresponds to the position of the nostril of the human body.

In one embodiment, two insertion columns 3 are provided and arranged in two nostrils respectively.

In one embodiment, the coconut powder is placed in a hollow cylindrical bag 5, one end of the hollow portion of the hollow cylindrical bag 5 has an opening, the other end of the hollow cylindrical bag is closed. The far-infrared generating tube 4 is directly sheathed through the opening of the hollow cylindrical bag when in use, and a new coconut powder sleeve is replaced in each time of use.

In one embodiment, the nasal alar part 2 is connected to the top end of the connecting part 1. Two nasal alar parts are provided, and fitted on both sides of the outer part of the nasal alar. As shown in FIG. 1, the nasal alar part 2 protrudes from the top position of the connecting part 1, which corresponds to the position of the nasal alar of the human body relative to the nostril. When in use, the nasal alar part 2 is folded at an angle along the dotted line in the drawing to fit over the nasal alar.

In one embodiment, the two ends of the connecting part 1 along the lateral corresponding direction of the nostril are provided with wearing fixing holes 6, which can be used for connecting the wearing string.

In one embodiment, it further includes an external control circuit, wherein the external control circuit is electrically connected with the far-infrared generating tube 4 and the ultrasonic generator, and is used for supplying power to the far-infrared generating tube 4 and the ultrasonic generator, and performing timed counting.

According to the treatment characteristics of sinusitis, nasal polyps and other diseases, the treatment cycle is long, the medication is inconvenient, the drugs cannot be attached, and the mechanism of the nervous system is too sensitive. In accordance with an embodiment of this present disclosure, the insertion column 3 is inserted into the nostril, and the control circuit is opened at the same time. At this time, the far-red light generator heats the powder and infrared treats the nasal cavity of a patient at the same time, and the medicine heated by the infrared light can bring the heated volatile substances into various parts of nasal tissue along with the breathing of the patient's nose. Low intensity pulsed ultrasound can accelerate drug atomization and promote tissue recovery, and infrared light and lauric acid play a complementary role in the treatment. At the same time, heated drugs, good effect absorption, and the nasal mucosa and other tissues of the stimulation is small.

According to years of clinical practice, the treatment effect is remarkable, one hour is treated each time. The treatment cycle is full for 30 days, and the recurrence rate in five years is extremely low.

The ultrasonic electronic rhinitis therapeutic apparatus with far-infrared atomized coconut essential oil provided by the disclosure is described in detail above, and the principles and embodiments of the disclosure are illustrated by specific examples, the descriptions of the above embodiments are only used for helping to understand the method and the core idea of the disclosure; meanwhile, for those skilled in the art, according to the idea of the present disclosure, there may be changes in the specific embodiments and the scope of application, to sum up, the content of this specification should not be construed as limiting the present disclosure.

The above description of the disclosed embodiments enables those skilled in the art to make or use the disclosure. Many modifications to these embodiments will be apparent to those skilled in the art, and the general principles defined herein can be implemented in other embodiments without departing from the spirit or scope of the present disclosure. Therefore, the present disclosure will not be limited to the embodiments shown herein, but will be accorded the widest scope consistent with the principles and novel features disclosed herein.

What is claimed is:

1. An ultrasonic electronic rhinitis therapeutic apparatus with far-infrared atomized coconut essential oil, comprising a nasal plug part and a nasal alar part;
   wherein the nasal plug part comprises an insertion column adapted to be disposed in a nostril; the insertion column is internally provided with coconut powder; a far-infrared generating tube is provided in the coconut powder;
   an ultrasonic generator is provided in the nasal alar part; and the nasal alar part is fitted on a lateral side of the nasal alar.

2. The apparatus of claim 1, wherein the far-infrared generating tube is provided at a middle position of the insertion column;
   part is adapted to be fitted and the two insertion columns are provided and arranged in two nostrils respectively.

3. The apparatus of claim 1, wherein the insertion column comprises a coconut powder sleeve; the coconut powder sleeve is a hollow cylindrical bag; the hollow cylindrical bag is filled with the coconut powder;
   and the far-infrared generating tube is provided at a hollow position of the hollow cylindrical bag.

4. The apparatus of claim 3, wherein a material of the hollow cylindrical bag comprises polyethylene terephthalate (PET) non-woven fabric, and is made by sealing and pressing with a sealing press, and is sleeved at the bottom of the far-infrared generating tube for packaging.

5. The apparatus of claim 1, wherein an outer surface of the far-infrared generating tube is coated with a graphene far-infrared film.

6. The apparatus of claim 5, wherein the bottom of the far-infrared generating tube is connected with a screw threaded base, and the screw threaded base is provided with a circuit connection point.

7. The apparatus of claim 1, wherein the nasal alar part further comprises a connecting part; the insertion column is provided vertically on the connecting part; the nasal alar part is connected to a top end of the connecting part; a second nasal alar part is provided; and the two nasal alar parts are adapted to be fitted on both sides of the outer part of the nasal alar.

8. The apparatus of claim 7, wherein two ends of the connecting part along a lateral corresponding direction of the nostril, during use, are provided with wearing fixing holes.

9. The apparatus of claim 1, further comprising an external control circuit; wherein the external control circuit is electrically connected with the far-infrared generating tube and the ultrasonic generator, and is configured to supply power to the far-infrared generating tube and the ultrasonic generator, and perform timed counting.

10. The apparatus of claim 1, wherein the ultrasonic electronic rhinitis therapeutic apparatus is used for atomizing an atomized grease and acid of the coconut powder, and the acid comprises lauric acid.

* * * * *